(12) United States Patent
Igarashi et al.

(10) Patent No.: US 11,554,124 B2
(45) Date of Patent: Jan. 17, 2023

(54) HEMATOPOIESIS-ENHANCING AGENT

(71) Applicant: TOHOKU UNIVERSITY, Miyagi (JP)

(72) Inventors: Kazuhiko Igarashi, Miyagi (JP); Hiroki Kato, Miyagi (JP); Yusho Ishii, Miyagi (JP); Chi Long Nguyen, Miyagi (JP); Hideo Harigae, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 65 days.

(21) Appl. No.: 16/975,439

(22) PCT Filed: Feb. 25, 2019

(86) PCT No.: PCT/JP2019/007121
§ 371 (c)(1),
(2) Date: Aug. 25, 2020

(87) PCT Pub. No.: WO2019/163994
PCT Pub. Date: Aug. 29, 2019

(65) Prior Publication Data
US 2021/0030765 A1 Feb. 4, 2021

(30) Foreign Application Priority Data
Feb. 26, 2018 (JP) .............................. JP2018-032469

(51) Int. Cl.
| | |
|---|---|
| *A61K 31/5517* | (2006.01) |
| *A61P 7/06* | (2006.01) |
| *A61K 31/196* | (2006.01) |
| *A61K 31/22* | (2006.01) |
| *C12N 5/0789* | (2010.01) |
| *C12Q 1/48* | (2006.01) |

(52) U.S. Cl.
CPC ........ *A61K 31/5517* (2013.01); *A61K 31/196* (2013.01); *A61K 31/22* (2013.01); *A61P 7/06* (2018.01); *C12N 5/0647* (2013.01); *C12Q 1/48* (2013.01); *C12N 2501/999* (2013.01)

(58) Field of Classification Search
CPC .................................................. C12N 5/0647
See application file for complete search history.

(56) References Cited

U.S. PATENT DOCUMENTS

2020/0022984 A1* 1/2020 Wang et al. ........... A61K 31/52

OTHER PUBLICATIONS

Maria L. Martínez-Chantar et al, L-Methionine Availability Regulates Expression of the Methionine Adenosyltransferase 2A Gene in Human Hepatocarcinoma Cells: Role of S-Adenosylmethionine*, Journal of Biological Chemistry, vol. 278, Issue 22 (Year: 2003).*

Hayashi et al., "S-Adenosylmethionine Synthetase is required for cell growth, Maintenance of G0 phase, and Termination of Quiescence of Fission Yeast", iScience, vol. 5, pp. 38-51, Jul. 27, 2018 (Year: 2018).*

Moore et al., DNA Methylation and its Basic Function, Neuropsychopharmacology Reviews, vol. 38, pp. 23-28, May 8, 2012 (Year: 2012).*

Shafqat, Naeem, et al., Insight into S-adenosylmethionine biosynthesis from the crystal structure of the human methionine adenosyltransferase catalytic and regulatory subunits, Biochem Journal (2013) (Year: 2013).*

Shima et al, S-adenosylmethionine Synthesis is Regulated by Selective N6-Adenosine Methylation and mRNA Degradation Involving METTL16 and YTHDC1, Cell Report, (Dec. 19, 2017) (Year: 2017).*

Bai, Jing, et al., Identification of a natural inhibitor of methionine adenosyltransferase 2A regulating one-carbon metabolism in keratinocytes, Elsevier, (Dec. 25, 2018) (Year: 2018).*

Carayon et al., "Involvement of peripheral Benzodiazepine Receptors in the Protection of Hematopoietic Cells Against Oxygen Radical Damage", Blood, vol. 87, No. 8, pp. 33710-3178, Apr. 15, 1996 (Year: 1996).*

Berge, Stephen M., et al. "Pharmaceutical Salts." J. Pharmaceutical Sciences. (Jan. 1977) vol. 66, No. 1, pp. 1-19 (Year: 1977).*

Koury, "Red blood cell production and kinetics", pp. 1-2, Apr. 15, 2016 (Year: 2016).*

Berge et al., "Revisiting a selection of target genes for the hematopoietic transcription factor c-Myb using chromatin immunoprecipitation and c-Myb knockdown", Blood Cells, Molecules, and Diseases, 2007, vol. 39, pp. 278-286.

Ramani et al., "Leptin Induces Mat2a and Mat2b Expression and Growth in Human Hepatocytes", Gastroenterology, Apr. 2006, vol. 130, No. 4, Suppl. 2, p. A-833, 2 pages total.

Langkamp-Henken et al., "Characterization of distinct forms of methionine adenosyltransferase in nucleated, and mature human erythrocytes and erythroleukemic cells", Biochimica et Biophysica Acta, 1994, vol. 1201, pp. 397-404.

Bacigalupo, A., "How I treat acquired aplastic anemia", Blood, 2017, vol. 129, No. 11, pp. 1428-1436.

(Continued)

*Primary Examiner* — Daniel R Carcanague
*Assistant Examiner* — Gillian A Hutter
(74) *Attorney, Agent, or Firm* — Wenderoth, Lind & Ponack, L.L.P.

(57) ABSTRACT

The purpose of the invention is to provide a novel hematopoiesis-promoting agent and a medicament comprising the hematopoiesis-promoting agent as an active ingredient for preventing or treating anemia, in particular refractory anemia. The present invention provides a hematopoiesis-promoting agent comprising an S-adenosylmethionine synthase inhibitor.

8 Claims, 12 Drawing Sheets

(56) References Cited

OTHER PUBLICATIONS

Almeida et al., "Recent advances in the treatment of lower-risk non-del(5q) myelodysplastic syndromes (MDS)", Leukemia Research, 2017, vol. 52, pp. 50-57.
Hester, Jr. et al., "1-(Aminoalkyl)-6-aryl-4H-s-triazolo[4,3-a][1,4]benzodiazepines with Antianxiety and Antidepressant Activity", J. Med. Chem., 1980, vol. 23, pp. 392-402.
Quinlan et al., "Targeting S-adenosylmethionine biosynthesis with a novel allosteric inhibitor of Mat2A", Nature Chemical Biology, 2017, vol. 13, No. 7, pp. 785-792, 9 total pages.
International Search Report dated Apr. 2, 2019 in International (PCT) Application No. PCT/JP2019/007121.

\* cited by examiner

HEMATOPOIESIS-ENHANCING AGENT

TECHNICAL FIELD

The present invention relates to a hematopoiesis-promoting agent, a medicament comprising the hematopoiesis-promoting agent for preventing or treating anemia, a method of producing hematopoietic cells by using the hematopoiesis-promoting agent, and the like. The present invention also relates to a method of screening for hematopoiesis-promoting agents in which a measured value of S-adenosylmethionine synthase activity is used as an indicator for the screening, a method of evaluating a hematopoiesis-promoting agent, and the like.

BACKGROUND ART

So far, there had not been any effective hematopoietic drug that directly stimulates erythropoiesis for treating refractory anemia such as aplastic anemia and myelodysplastic syndrome. The only therapies that could potentially be applied for such disorders, such as immunosuppressive therapy, chemotherapy, and hematopoietic stem cell transplantation, pose an increased risk of inducing complications. Additionally, there are a number of cases that are resistant to the aforementioned therapies or are not applicable for those therapies because of factors such as the age of the subject to be treated (Non-patent Documents 1 and 2). A certain effectiveness of an erythropoietin formulation, which is known as a hematopoiesis-promoting agent, has been observed previously in treatment for renal anemia, but such an effect cannot be expected in case of anemia associated with a hematologic disease in which endogenous erythropoietin production has already been promoted. As a consequence, a considerable number of patients may need red blood cell transfusion, which is one of the most effective palliative treatment. However, such treatment poses problems including cost increase associated with long term treatment and organ dysfunction induced by iron overload. Therefore, one of the goals of this therapy is to eliminate transfusion dependence in patients who are receiving refractory anemia treatment.

Meanwhile, an inhibitor of MAT, i.e., S-adenosylmethionine synthase, is considered as a candidate for anticancer drug (Non-patent Documents 3 and 4). However, the hematopoietic effect of the S-adenosylmethionine synthase inhibitor had not been known previously.

Prior Art References

Non-Patent Documents

Non-patent Document 1: Bacigalupo A., Blood 2017 Mar. 16; 129(11):1428-1436

Non-patent Document 2: Almeida A et al., Leuk Res 2017 January; 52:50-57

Non-patent document 3: Jackson B. Hester, Jr., J. Med. Chem. 1980, 23, 392-402

Non-patent Document 4: Casey L Quinlan et al., Nature Chemical Biology 13, 785-792 (2017)

SUMMARY OF THE INVENTION

The present invention was achieved in view of the above circumstances of the related art. An aspect of the present invention is to provide a novel hematopoiesis-promoting agent and a medicament comprising the hematopoiesis-promoting agent as an active ingredient for preventing or treating anemia, particularly refractory anemia.

S-adenosylmethionine synthase MAT (two isozymes thereof, designated as MAT1 and MAT2, have been identified, and MAT2 being consisted of two subunits, MAT2A and MAT2B) synthesizes S-adenosylmethionine, a donor of methyl group, from ATP and methionine. This enzyme plays an important role in mechanisms such as epigenetic modification. The present inventors have obtained findings that cycloleucine (CLEU) which serves as a MAT inhibitor induces a notable promotion of the maturation of mouse bone marrow erythroblasts and a significant increase in peripheral blood hemoglobin level. The present invention was accomplished based on these findings. More specifically, the present invention provides a novel therapeutic drug for anemia associated with hematologic disease, which had been difficult to be treated with conventional hematopoiesis-promoting agents. Furthermore, the present invention provides a high throughput screening system for searching a novel hematopoiesis-promoting agent, in which various hit compounds targeting MAT and being more clinically applicable are identified, followed by developing lead compounds from the hit compound. The present invention also provides a novel hematopoiesis-promoting agent.

More specifically, the gist of the present invention is as follows:

[1] A hematopoiesis-promoting agent comprising an S-adenosylmethionine synthase inhibitor.

[2] The hematopoiesis-promoting agent according to [1], wherein the S-adenosylmethionine synthase is MAT2A.

[3] The hematopoiesis-promoting agent according to [1] or [2], wherein the S-adenosylmethionine synthase inhibitor is selected from the group consisting of cycloleucine, a derivative thereof, a derivative of 4H-s-triazolo[4,3-a][1,4]benzodiazepine, and a pharmaceutically acceptable salt thereof.

[4] The hematopoiesis-promoting agent according to [1] or [2], wherein the S-adenosylmethionine synthase inhibitor is selected from the group consisting of 3-acetyl-11-keto-β-boswellic acid, a derivative thereof, and a pharmaceutically acceptable salt thereof.

[5] A medicament for preventing or treating anemia comprising the hematopoiesis-promoting agent according to any one of [1] to [4].

[6] A method of producing hematopoietic cells, comprising the step of:
- culturing hematopoietic progenitor cells in the presence of the hematopoiesis-promoting agent according to any one of [1] to [4].

[7] A method of screening for a hematopoiesis-promoting agent, comprising the steps of:
- measuring S-adenosylmethionine synthase activity in the presence or absence of a candidate of the hematopoiesis-promoting agent; and
- selecting a candidate that lowers the measured value of the S-adenosylmethionine synthase activity in the presence of the candidate of the hematopoiesis-promoting agent than in the absence thereof.

[8] A method of evaluating a hematopoiesis-promoting agent, comprising the steps of:
- measuring S-adenosylmethionine synthase activity in the presence of a hematopoiesis-promoting agent to be evaluated; and
- evaluating the hematopoiesis-promoting effect of the hematopoiesis-promoting agent to be evaluated by using the measured value of the S-adenosylmethionine synthase activity in the presence of the hematopoiesis-promoting agent to be evaluated as an indicator for evaluation.

[9] A method of promoting hematopoiesis comprising:
administering an S-adenosylmethionine synthase inhibitor to a subject in need of promoting the hematopoiesis thereof.

[10] An S-adenosylmethionine synthase inhibitor for use in promoting hematopoiesis.

According to the present invention, it is possible to provide a hematopoiesis-promoting agent having a superior hematopoiesis promoting effect, which acts through a mechanism of action completely different from that of erythropoietin, the conventional hematopoiesis-promoting agent. Furthermore, according to the present invention, it is also possible to provide a medicament for preventing or treating anemia, particularly refractory anemia.

EMBODIMENTS FOR CARRYING OUT THE INVENTION

Figure 1:
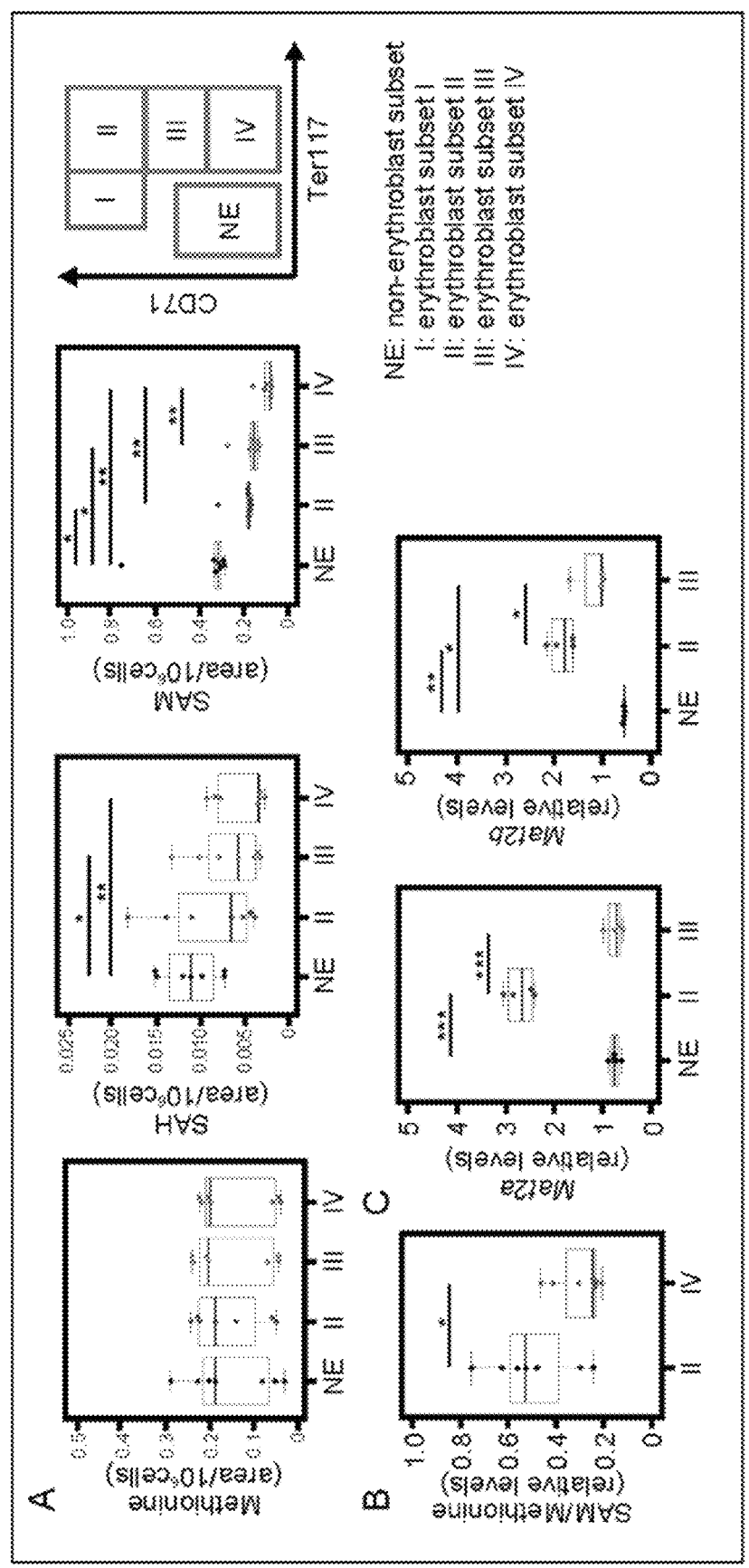
FIG. 1 is the experimental result showing that SAM (S-adenosylmethionine) synthesis is down-regulated during the maturation of erythroblasts. Panel A: Abundance of methionine, SAH (S-adenosylhomocysteine), and SAM in each subset of cells sorted from bone marrow. These abundances were quantitatively analyzed by mass spectrometry. Panel B: Ratio of SAM to methionine in each of the subsets. The abundances of SAM and methionine in each of the samples were corrected to the abundances in non-erythroblast subsets. Panel C: RNA expression levels of MAT2A and MAT2B analyzed by RT-PCR. Expression levels were normalized to Actb. Each point shown on the box plot represents an individual mouse sample. Asterisks correspond to p values: *$P<0.05$, $P<0.01$, and *$P<0.001$.

The present invention will be described as follows.
The main abbreviations used in this specification are as follows:
MAT: methionine adenosyltransferase (S-adenosylmethionine synthase)
EPO: erythropoietin
SAM: S-adenosylmethionine
SAH: S-adenosylhomocysteine
CLEU: cycloleucine
AKBA: 3-acetyl-11-keto-β-boswellic acid (CAS Number: 67416-61-9).

Hematopoiesis-Promoting Agent

One aspect of the present invention relates to a hematopoiesis-promoting agent comprising an S-adenosylmethionine synthase inhibitor. As mentioned above, the hematopoiesis-promoting agent of the present invention exerts its hematopoiesis-promoting action via the S-adenosylmethionine synthase inhibitor contained therein.

The term "S-adenosylmethionine synthase" as used herein is not particularly limited to a specific enzyme as long as it catalyzes biosynthesis from methionine and ATP as substrates to S-adenosylmethionine. In addition, "S-adenosylmethionine synthase" may also be referred generally as "S-adenosylmethionine synthetase", "adenosylmethionine synthase" or "methionine adenosyl transferase", but they can be used interchangeably in this specification.

Specifically, examples of S-adenosylmethionine synthase include MAT I/III (MAT I/III is consisted of the active subunit MAT1A, and may also be referred generally as "MAT1A," but both of which can be used interchangeably in this specification), and MAT II (MAT II is consisted of the active subunit MAT2A and the regulatory subunit MAT2B, and may also be referred generally as "MAT2A" or "MAT2," but both of which can be used interchangeably in this specification). Preferably, the S-adenosylmethionine synthase is MAT2A.

Also, the term "methionine" as used herein refers to, unless otherwise specified, L-methionine.

Also, the term "S-adenosylmethionine synthase inhibitor" as used herein is not particularly limited to a specific inhibitor as long as it has an inhibitory effect on the S-adenosylmethionine synthase in a mammal. Preferably, the S-adenosylmethionine synthase inhibitor is a substance having an inhibitory effect on the S-adenosylmethionine synthase in either mammalian cells (preferably, hematopoietic stem cells, myeloid progenitor cells erythroid progenitor cells, proerythroblasts, erythroblasts, and the like). The inhibitory mechanism of action of S-adenosylmethionine synthase is not particularly limited, but may be that: the repression of the expression of S-adenosylmethionine synthase at any stage of the expression thereof, such as gene transcription of S-adenosylmethionine synthase, posttranscriptional regulation, translation, or post-translational modification; enzyme inhibition such as inhibition of the expression of S-adenosylmethionine synthase protein other than those described above, competitive inhibition, noncompetitive inhibition such as the inhibition of association between subunits, uncompetitive inhibition, and the like.

As described above, on the basis of the fact that a strong correlation between S-adenosylmethionine synthase inhibitory effect and hematopoiesis-promoting effect was confirmed, it is now possible to perform screening of various S-adenosylmethionine synthase inhibitor by using the S-adenosylmethionine synthase activity as an indicator of the promotion of hematopoiesis, to thereby identify an S-adenosylmethionine synthase inhibitor that can be used as the hematopoiesis-promoting agent. In other words, the S-adenosylmethionine synthase inhibitor is not particularly limited to a specific compound as long as it has MAT inhibitory effect, but may be low molecular compounds, peptides, antibodies, nucleic acids (antisense oligonucleotides including siRNA), extracts. The S-adenosylmethionine synthase inhibitor may be a compound known as an S-adenosylmethionine synthase inhibitor or may be a compound identified by the screening. Specifically, examples of the S-adenosylmethionine synthase inhibitor include, but not limited to, cycloleucine and a derivatives thereof, a derivative of 4H-s-triazolo[4,3-a][1,4]benzodiazepine, 3-acetyl-11-keto-β-boswellic acid and a derivatives thereof, or a salt thereof. The S-adenosylmethionine synthase inhibitor may be commercially available or may be synthesized by means of usual organic synthesis approach. The S-adenosylmethionine synthase inhibitor may be used singly or may be used in combination of two or more thereof.

The derivative of cycloleucine refers to a reactive compound which has been chemically derived from cycloleucine and exhibits the same effect as cycloleucine in human body. Examples of such derivative of cycloleucine include, but not limited to, N-Boc-L-valine, 3-aminopropionic acid, 3-(carboxymethyl)-2-(2-pentenyl)cyclopentanone, D-proline, other unnatural amino acids. Pharmaceutically non-toxic compounds with no or little side effects to human body are preferred. Examples of the derivative may also include a prodrug of cycloleucine. Examples of a derivative of 4H-s-triazolo[4,3-a][1,4]benzodiazepine include, but not limited to, PF9366 (2-(7-chloro-5-phenyl-[1,2,4]triazolo[4,3-a]quinolin-1-yl)-N,N-dimethylethan-1-amine)(Non-patent Documents 3 and 4). Examples of the derivative of 3-acetyl-11-keto-β-boswellic acid include, but not limited to, 11-keto-β-boswellic acid and compounds disclosed in the literature such as Mediterranean Journal of Chemistry 2017, 6(5), 180-190, Nat Prod Res. 2019 Jan. 29:1-8, Anticancer Agents Med Chem. 2017; 17(8):1153-1167.

Further examples of the S-adenosylmethionine synthase inhibitor include fluorinated N,N-dialkylamino stilbene compounds described in Zhang et al, ACS Chem Biol, 2013, 8(4): 796-803; 2',6'-dihalostilylaniline described in Sviripa et al, J Med Chem, 2014, 57: 6083-6091; pyridine or pyrimidine compounds; compounds described in WO 2012103457.

Specific examples of the pharmaceutically acceptable salt include, but not limited to, inorganic salt (sodium salt, potassium salt, lithium salt; calcium salt, magnesium salt; aluminum salt, iron salt, zinc salt, copper salt, nickel salt, cobalt salt; ammonium salt, and the like), various organic salt, hydrohalogenic acid salts, inorganic acid salts, organic acid salts, and amino acid salts.

Figure 11:
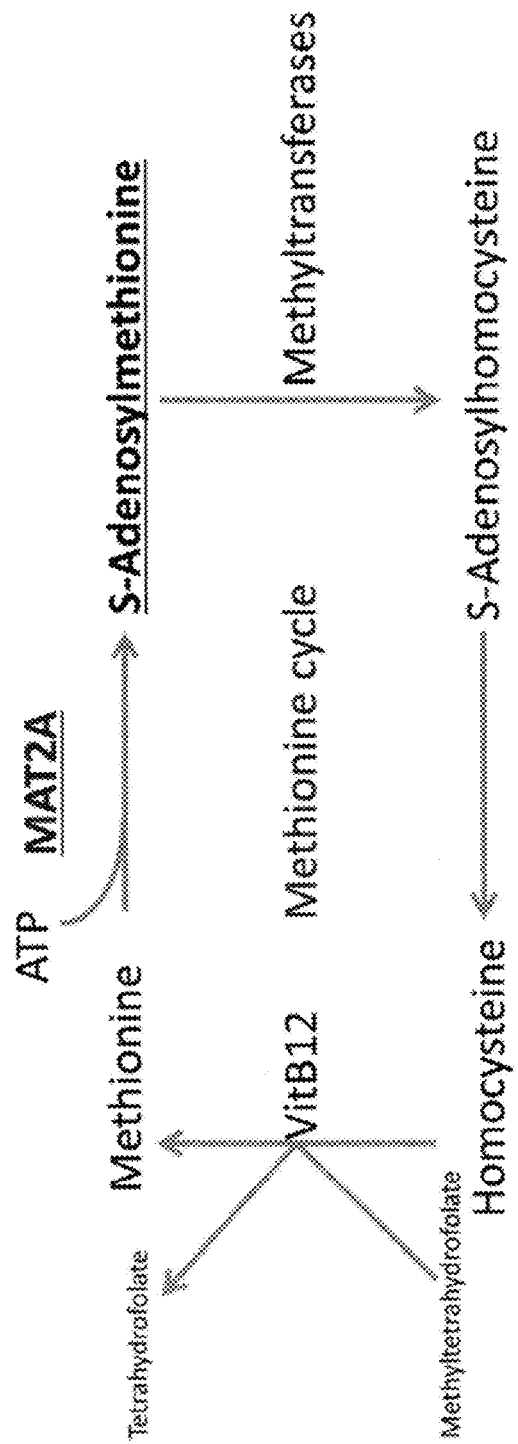
FIG. 11 is a schematic diagram of methionine cycle.

The measurement of the S-adenosylmethionine synthase inhibitory activity can be performed in accordance with known methods. For example, it may be measured by means of in vitro enzyme activity assay system. Specifically, the MAT2A inhibitory activity (hereinafter, description will be made with regards to MAT2A as a representative example of S-adenosylmethionine synthase) in the S-adenosylmethionine synthesis reaction from ATP and methionine can be measured (FIG. 11). In other words, as a non-limiting example, the enzymatic activity of MAT2A is assessed by use of an assay system such as a luciferase assay system, in which the concentration of ATP remained after the above-described reaction is determined, and the inhibitory activity of the analyte of interest is estimated based the thus-obtained concentration. As a positive control of the inhibitor, cycloleucine may be used.

The S-adenosylmethionine synthase inhibitor employed in the present invention is not particularly limited, but a substance having $IC_{50}$ against S-adenosylmethionine synthase activity of, for example, 10 mM or less, 1 mM or less, 100 μM or less, or 10 μM or less may preferably be used.

The term "promotion of hematopoiesis" as used herein means that, administration of an S-adenosylmethionine synthase inhibitor causes induction of differentiation from hematopoietic progenitor cells (bone marrow progenitor cells, erythroid progenitor cells, proerythroblasts, erythroblasts etc.) to hematopoietic cells (proerythroblasts erythroblasts, red blood cells, etc.), and as a result of that, alterations such as an increase in the number of hematopoietic cells or an improvement of a numerical value corresponding to the increase in the number of hematopoietic cells are observed after administration of the S-adenosylmethionine synthase inhibitor as compared to those before administration thereof. Hematopoiesis-promoting effect may be measured by a conventional biological approach such as blood cell count measurements or flow cytometry, or a molecular biological technique, or the like. The term "having hematopoiesis-promoting activity" as used herein may refer to the fact that the number of hematopoietic cells increases with respect to a control (i.e., in the absence of a hematopoiesis-promoting agent) to, for example, 1.2 to 50 fold, preferably 1.2 to 5 fold, more preferably 1.2 to 1.5 fold, but not limited thereto.

Medicament, Food and Beverage

Further aspect of the present invention relates to a medicament for preventing or treating anemia comprising the hematopoiesis-promoting agent of the present invention. As mentioned above, on the basis of the fact that the hematopoiesis-promoting agent of the present invention exhibits hematopoiesis-promoting activity through the induction of the differentiation from hematopoietic progenitor cells to hematopoietic cells, it can suitably be used as a medicament for preventing or treating disorders associated with conditions such as blood loss or decreased hematopoiesis function. Also, it may be suitably used for the purposes such as for ameliorating decreased hematopoiesis function (including prevention of the aforementioned disorders), for food and beverage for daily intake, or for a reagent for research purpose.

Now, as described hereinafter in Example section, the S-adenosylmethionine synthase inhibitor may be considered as a novel hematopoiesis-promoting agent that acts through a mechanism of action completely different from that of the existing hematopoiesis-promoting agent, i.e., erythropoietin formulation. Considering that many of those who are afflicted with refractory anemia associated with hematologic disease are erythropoietin-resistant, the present findings that inhibition of S-adenosylmethionine synthase may promote erythropoiesis are expected to contribute a considerable reduction of complications associated with transfusion dependence as well as social costs.

Examples of the disorder associated with blood loss or decreased hematopoiesis function are not particularly limited, but include renal anemia (preferably erythropoietin-resistant renal anemia), iron deficiency anemia, anemia associated with therapy using anti-cancer drug, refractory anemia (aplastic anemia, myelodysplastic syndrome, myelofibrosis, pure red-cell aplasia, paroxysmal nocturnal hemoglobinuria, autoimmune hemolytic anemia, congenital bone marrow failure syndrome, etc.), hemolytic anemia, blood loss anemia.

The medicament of the present invention may be formulated in pharmaceutical formulations in various forms by known pharmaceutical methods. It can be formulated and used in a formulation of dosage form suitable for oral administration, intraperitoneal administration, transdermal administration, subcutaneous administration, intravenous administration, inhalation administration, or the like. In formulating the pharmaceutical formulation, various pharmaceutically acceptable carriers, for example, excipients, disintegrants, lubricants, binders, surfactants, fluidity improvers, colorants, and flavorants may be used in combination as appropriate.

Also, the food and the beverage of the present invention may be prepared in the form of various food and beverages by known methods for producing food and beverage products. A known pharmaceutical component used for preventing or treating of anemia may also be combined in the medicament and food and beverage of the present invention. Furthermore, any known pharmaceutically active ingredient other than those described above may also be incorporated therein.

The hematopoiesis-promoting agent, the medicament and the food and the beverage of the present invention may be used for a mammalian subject such as human and for a non-human animal. The non-human animal subject is not particularly limited, but may be various domestic animals, poultry, pets, laboratory animals.

The amount of the hematopoiesis-promoting agent, the medicament, the food, and the beverage of the present invention to be administered or ingested is appropriately selected depending on the factors such as age, body weight, symptom, or health condition of the subject, or type of composition (such as medicament, food and beverage). The amount per one dose of the hematopoiesis-promoting agent, the medicament, and the food and beverage to be administered or ingested is not particularly limited, but a hematopoiesis-promoting agent is administered in an amount, for example, of from 0.01 mg/kg body weight to 1000 mg/kg body weight.

A further aspect of the present invention relates to a method of promoting hematopoiesis of a subject, comprising administering or causing to be ingested to the subject a hematopoiesis-promoting agent, a medicament, or food and beverage of the present invention. Another aspect of the present invention relates to a method of preventing or treating anemia of a subject, comprising administering or causing to be ingested to the subject a hematopoiesis-promoting agent, a medicament, or food and beverage of the present invention.

Production Method

A further aspect of the present invention relates to a method of producing hematopoietic cells, comprising culturing hematopoietic progenitor cells in the presence of a hematopoiesis-promoting agent of the present invention. This method is, in other words, a method of inducing differentiation for hematopoietic cells, comprising the step of culturing hematopoietic progenitor cells in the presence of a hematopoiesis-promoting agent of the present invention.

Examples of the hematopoietic progenitor cells include myeloid progenitor cells, erythroid progenitor cells, proerythroblasts, and erythroblasts. Hematopoietic progenitor cells employed are not limited to those derived from animals, but may also be those derived from differentiation of cells such as iPS cells. The culturing method employed in the method of producing hematopoietic cells of the present invention is not particularly limited except for the addition of the hematopoiesis-promoting agent of the present invention, and any conventional method of cell culture is possible as long as it allows maintaining and survival of hematopoietic progenitor cells (preferably myeloid progenitor cells, erythroid progenitor cells, proerythroblasts, erythroblasts) and red blood cells, as well as maintaining, survival, and differentiation of the hematopoietic progenitor cells during culture.

The culture medium for the hematopoietic progenitor cells is not particularly limited, but examples include, MEMα, DMEM, RPMI-1640, Ham's F-12, and IMDM. Additives such as those used customarily in cell culture may be used in the culture medium without limitation, provided that they do not adversely affect the advantageous effect of the present invention. In particular, it is preferable to use serum or a serum substitute. Examples of further additive include 2-mercaptoethanol, sodium pyruvate, amino acids, antibiotics, and N-acetyl cysteine.

To the culture medium of hematopoietic progenitor cells is added an S-adenosylmethionine synthase inhibitor, i.e., the hematopoiesis-promoting agents of the present invention, as a differentiation inducer for hematopoietic cells. The concentration of the hematopoiesis-promoting agent in the culture medium may appropriately be modified depending on the factors such as cell source, number of cells, and quantity of culture medium. The concentration is not particularly limited, but is typically from 1 to 10,000 μg/mL, preferably from 1 to 5000 ng/mL, approximately.

The incubator used for the cell culture is not particularly limited if it is customary used for animal cell culture. Examples of the incubation condition include, at a temperature of from 37° C. to 39° C., under atmosphere of 5% carbon dioxide and 95% air, and under high humidity. Any incubator capable of setting such conditions may be used.

It is preferable to replace a portion of the culture medium with a fresh one every 2 to 4 days during the incubation period. The incubation period may be modified depending on the animal species used and the condition of the cells collected, but generally it lasts for a few days to a week.

It is also preferable to confirm during or after the culture if the differentiation for hematopoietic cells have been induced by a technique such as blood cell counts or flow cytometry. It is also possible to modify the incubation period depending on the degree of differentiation induced for hematopoietic cells.

Screening Method

A further aspect of the present invention is a method of screening for an S-adenosylmethionine synthase inhibitor, comprising the steps of: measuring S-adenosylmethionine synthase activity in the presence or absence of a candidate of the S-adenosylmethionine synthase inhibitor; and selecting a candidate that lowers the measured value of the S-adenosylmethionine synthase activity in the presence of the candidate of the S-adenosylmethionine synthase inhibitor than in the absence thereof.

A further aspect of the present invention relates to a method of screening for a hematopoiesis-promoting agent, comprising the steps of: measuring S-adenosylmethionine synthase activity in the presence or absence of a candidate of a hematopoiesis-promoting agent; and selecting a candidate that lowers the measured value of the S-adenosylmethionine synthase activity in the presence of the candidate of the hematopoiesis-promoting agent than in the absence thereof. It means that, on the basis of the fact that a strong correlation between S-adenosylmethionine synthase inhibitory effect and hematopoiesis-promoting effect has been confirmed, as described above, the S-adenosylmethionine synthase activity can be used as an indicator for screening hematopoiesis-promoting agents. The step of "measuring S-adenosylmethionine synthase activity in the presence or absence of a candidate of the S-adenosylmethionine synthase inhibitor (or hematopoiesis-promoting agent)" may be performed in a manner in which S-adenosylmethionine synthase is expressed in the presence or absence of the candidate of the S-adenosylmethionine synthase inhibitor (or hematopoiesis-promoting agent), followed by measuring the expression level of the S-adenosylmethionine synthase or S-adenosylmethionine synthase activity.

As used herein, the phrase "lowers the measured value of the S-adenosylmethionine synthase activity in the presence of the candidate of the S-adenosylmethionine synthase inhibitor (or hematopoiesis-promoting agent) than in the absence thereof" means that, for example, the measured value of the S-adenosylmethionine synthase activity in the presence of the candidate of the S-adenosylmethionine synthase inhibitor (or hematopoiesis-promoting agent) is lower by 50%, 40%, 30%, 20%, or 10% than the measured value in the absence of the candidate of the S-adenosylmethionine synthase inhibitor (or hematopoiesis-promoting agent), but are not limited thereto.

For example, in the method of measuring the S-adenosylmethionine synthase activity, in vitro enzyme activity assay system may be used for the measurement.

Specifically, an inhibitor of MAT2A (hereinafter, description will be made with regards to MAT2A as a representative example of the S-adenosylmethionine synthase) may be identified by using the S-adenosylmethionine synthesis reaction from ATP and methionine (FIG. 11). As a specific example, although not limited thereto, the enzymatic activity of recombinant mouse MAT2A after addition of a candidate of the hematopoiesis-promoting agent is measured by use of an assay system such as luciferase assay system, so as to determine the concentration of ATP remained after the aforementioned reaction has occurred, to thereby evaluate the inhibitory activity of the candidate. Compounds having MAT2A inhibitory activity can be identified through a high-throughput screening system according to the present method.

Since MAT2A synthesizes S-adenosylmethionine from methionine and ATP, the inhibitory effect can be evaluated based on the amount of ATP remained in the test tube. The amount of ATP is determined by the activity of ATP-dependent enzyme, luciferase. Herein either natural or recombinant MAT2A may be used, however, the present inventors have already construct recombinant MAT2A. Moreover, high-throughput screening in 384-well plates using the luciferase assay system is widely used. Thus, it is considered that the screening system for the present invention may readily be established. As the positive control of the inhibitor, e.g., cycloleucine, PF9366, 3-acetyl-11-keto-β-boswellic acid may be used. It is also preferable to confirm hematopoiesis promoting activity and safety of the hematopoiesis-promoting agent after the hematopoiesis-promoting agent is identified by the screening. As the method of measuring the hematopoiesis promoting activity, for example, the method of measuring the hematopoiesis-promoting effect as describe above may be applied.

Evaluation Method

A further aspect of the present invention relates to a method of evaluating a hematopoiesis-promoting agent, comprising the steps of: measuring S-adenosylmethionine synthase activity in the presence of the hematopoiesis-promoting agent to be evaluated; and evaluating the hematopoiesis-promoting effect of the hematopoiesis-promoting agent by using the measured value of the S-adenosylmethionine synthase activity in the presence of the hematopoiesis-promoting agent to be evaluated as an indicator for evaluation. It means that, on the basis of the fact that a strong correlation between S-adenosylmethionine synthase inhibitory effect and hematopoiesis promoting effect has been confirmed, as described above, the S-adenosylmethionine synthase activity can be used as an indicator to evaluate the presence or absence or degree of the hematopoiesis promoting effect of the hematopoiesis-promoting agent to be evaluated.

As the method of measuring the S-adenosylmethionine synthase activity, the method described above for carrying out the screening method of the present invention may be applied. As the positive control of the inhibitor, for example, cycloleucine, PF9366, 3-acetyl-11-keto-β-boswellic acid may be used.

EXAMPLES

Hereinafter, the invention will be described more specifically with reference to Examples, but it is not limited thereto as long as it does not deviate from the gist of the present invention.

Materials and Methods

Mouse

Wild-type mice with a genetic background of C57BL/6J were purchased from Charles River Laboratories, Inc. Mice at 8 to 14 weeks of age were used for analysis. For CLEU treatment (50 mg/body), a solution of cycloleucine (CLEU) was prepared by diluting cycloleucine (CLEU) (Sigma) in PBS (50 mg/ml), and 1 ml of the CLEU solution was administered intraperitoneally. For AKBA treatment (2 mg/body), 2 mg AKBA (Enzo Life Sciences)/20% DMSO/1 mL PBS solution was administered intraperitoneally. Vehicle without AKBA was used as a control. For measuring complete blood count of peripheral blood, peripheral blood was collected from facial veins and counted by use of an automated animal blood cell counter (microsemi LC-662). All of the experiments conducted in this study were approved by the Animal Experiment Committee of the Environmental Safety Committee of Tohoku University.

Flow Cytometry and Cell Sorting

BM cells and spleen cells were harvested in a conventional manner. Cells were stained with combinations of antibodies specific to erythroblasts and mature cells, to thereby identify them. The cells were visualized with antibody and streptavidin-peridinin chlorophyll protein-cyanin 5.5. The antibodies used in this study were as follows: anti-CD3e (145-2C11), anti-CD4 (GK1.5 or RM4.5), anti-CD8a (53-6.7), anti-Gr-1 (RB6-8C5), anti-B220 (RA3-6B2), anti-Ter-119 (TER-119), anti-CD71 (R17217 or C2). Cells were stained with DAN (Sigma), and dead cells were excluded from analysis. Flow cytometric analysis and cell sorting were performed according to the manufacturer's protocol using FACS AriaII (BD), and then the obtained data were analyzed using FlowJo software (TreeStar).

RNA Sequence Data Sampling and Analysis

Total RNA was isolated by using the RNeasy kit (Qiagen) from the sorted sample of bone marrow subset II erythroblasts (PBS; n=4, CLEU; n=4). The quality of the isolated RNA (RIN>0.8) was checked using a 2100 bioanalyzer (Agilent), and 250 ng of the RNA was used as input for library preparation in accordance with the manufacturer's instructions using the TruSeq Stranded mRNA Library Prep Kit (Illumina). High-throughput sequencing (51 bp, single-ended) was performed using Hiseq2500 Rapid mode v2 (Illumina). Sequenced reads were mapped to the reference mouse genome (mm9) by using bowtie2 version 2.2.5 and tophat version 2.1.0, and then the abundances of transcripts were estimated by using cufflinks version 2.2.1. Gene expression levels were normalized to the average of fragments per kilobase of transcript per million mapped reads (FPKM) value. Individually expressed genes with FPKM>10 and CV<0.5 (under at least one of the two conditions) were used for further analysis ($\log_2$ FC<−0.5 or $\log_2$ FC>0.5, P<0.05 within each condition). DAVID 6.8 web tool was used to find gene ontology terms enriched in significantly up- or down-regulated genes.

Whole Genome Bisulfite Sequencing (WGBS) Data Sampling and Analysis

DNA was isolated by using phenol/chloroform extraction from sorted sample of bone marrow subset II erythroblasts (PBS; n=2, CLEU; n=2). DNA quality control, bisulfite conversion, library preparation, high-throughput sequencing, and data mapping were performed at Macrogen, Inc. Briefly, TruSeq DNA Methylation Kit and EZ DNA Methylation Gold (Illumina and Zymo Research) were used for library preparation according to the manufacturer's protocol (TruSeq DNA Methylation Library Preparation Guide), followed by high-throughput sequencing by HiseqX (Illumina). After the sequencing run, the raw sequence reads were filtered based on quality, and the adapter sequences were trimmed off. The remaining reads are mapped to the reference genome (mm9) using BSMAP based on SOAP (Short Oligo Alignment Program). SAMBAMBA version 0.5.9 was used to remove index and PCR duplicates, and to select reads with modification. Methylation level was calculated for every single cytosine from mapping results using BSMAP version 2.87. Only cytosine positions with >=5 reads coverage were used for further analysis.

In Vitro Erythroid Differentiation of Human $CD34^+$ Umbilical Cord Blood Cells

Human $CD34^+$ umbilical cord blood cells were obtained from the Kanto Koshinetsu Block Blood Center (Tokyo, Japan). The use of cord blood samples for research purposes was approved by the Tohoku University Ethics Committee. The technical details of this method have been described previously. Briefly, $CD34^+$ umbilical cord blood cells were cultured in growth medium for 5 days, and subsequently, the cells ($1\times10^5$/ml) were cultured in differentiation medium for 7 days. For treatment with CLEU, the concentration thereof was 2.5 mg/ml. As the growth medium, StemMACS HSC Expansion Media XF, human (MACS), supplemented with StemMACS HSC Expansion Cocktail, human (MACS) was used. As the differentiation medium, StemSpan SFEM (STEMCELL) supplemented with hSCF (100 ng/ml; Peprotech), hFLT3-L (33.3 ng/ml; Peprotech), hIL3 (13.3 ng/ml; Peprotech), hBMP4 (13.3 ng/ml; Peprotech), hEPO (2.67 IU/ml; Kyowa Kirin Co., Ltd.), and hydrocortisone (1 μM; Sigma) was used.

The present inventors hypothesized as follows. Epigenetic modifications play a central role in blood cell development. Maturation of erythroblasts is a dynamic process during which significant morphological changes of erythroblasts involving nuclear condensation and enucleation occur. To date, it has been shown that global DNA demethylation and post-translational histone modifications occur during the maturation of erythroblasts. Therefore, proper epigenetic modifications are essential for the maturation of erythroblasts. S-adenosylmethionine (SAM) as a potent methyl donor is required to establish DNA and histone methylation. Accordingly, SAM and methionine adenosyltransferase (MAT) which catalyzes the synthesis of SAM from methionine and ATP play an important role in the maturation of erythroblasts. However, little is known about the function of these factors in this process. Accordingly, the present inventors conducted the following experiments to clarify the function of these factors.

Example 1

Change in abundances of SAM-related metabolites during the maturation of erythroblasts in bone marrow (BM) was investigated. It was shown, by mass spectrometry, that methionine and related amino acids did not change significantly, but the abundance of SAM was progressively decreased during the maturation of erythroblasts (Panel A of FIG. 1). Therefore, it was assumed that SAM synthesis was decreased during the maturation of erythroblasts (Panel B of FIG. 1). MAT2A and its cofactor MAT2B, the primary isozymes of MAT in tissue other than liver, were decreased consistently during the maturation of erythroblasts (Panel C of FIG. 1). It means that SAM synthesis is negatively regulated during the maturation of erythroblasts.

Example 2

Figure 6:
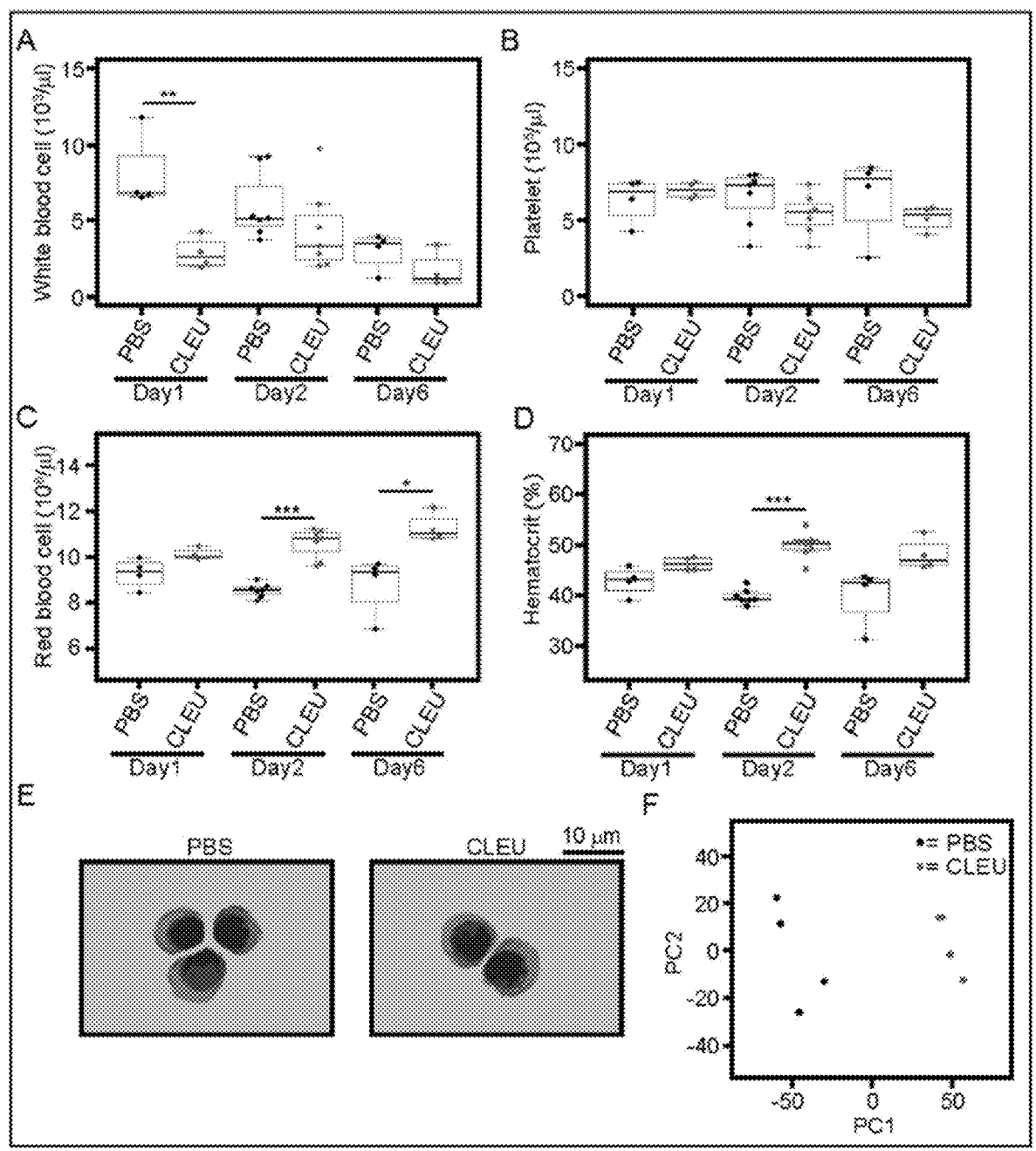
FIG. 6 is the experimental result showing complete blood cell count of CLEU or PBS treated mouse. Panels A to D: Complete peripheral blood cell count (CBC) of CLEU or PBS treated mouse (Days 1-6). Panel A: White blood cell count ($10^3/\mu L$). Panel B: Platelet count ($10^5/\mu L$). Panel C: Red blood cell count ($10^6/\mu L$). Panel D: Hematocrit (%). Panel E: Images (photographs) of May-Giemsa stained nucleated cells selected from bone marrow erythroblast subset II harvested from PBS or CLEU treated mouse (Day 2). Panel F: Principle component analysis (PC) of RNA sequencing data shown in Panel A of FIG. 3.

Next, in order to clarify the importance of SAM in erythropoiesis, mice were treated with the MAT inhibitor, cycloleucine (CLEU; 50 mg/body). It showed that CLEU actually had an ability to reduce the abundance of SAM present in erythroblasts (Panel A of FIG. 2). There were no particularly consistent differences in white blood cell counts and in platelet counts, but surprisingly, there was a marked increase in hemoglobin levels, red blood cells, and hematocrit by CLEU treatment (Panel B of FIG. 2 and Panels A-D of FIG. 6). BM cell counts were significantly increased and BM color had changed to redder by CLEU treatment (Panels C-D of FIG. 2). Through flow cytometric analysis, it was revealed that this phenotype was caused by the considerable increase of erythroid cells in BM (Panels E-F of FIG. 2). Through Ter119/CD71 double staining, it was also revealed that the increase of erythroblasts was initiated from subset II and that the maturation of erythroblasts was significantly up-regulated by CLEU treatment (Panels G-I of FIG. 2). These findings are also supported by pathological findings in BM and peripheral blood (Panels J-K of FIG. 2)). Interestingly, serum erythropoietin levels were significantly down-regulated by CLEU treatment (Panel L of FIG. 2). This could be caused by negative feedback regulation. To summarize these results, CLEU treatment significantly promotes the maturation of erythroblasts in BM in an erythropoietin-independent manner and reduces SAM synthesis and erythropoietin.

Figure 10:
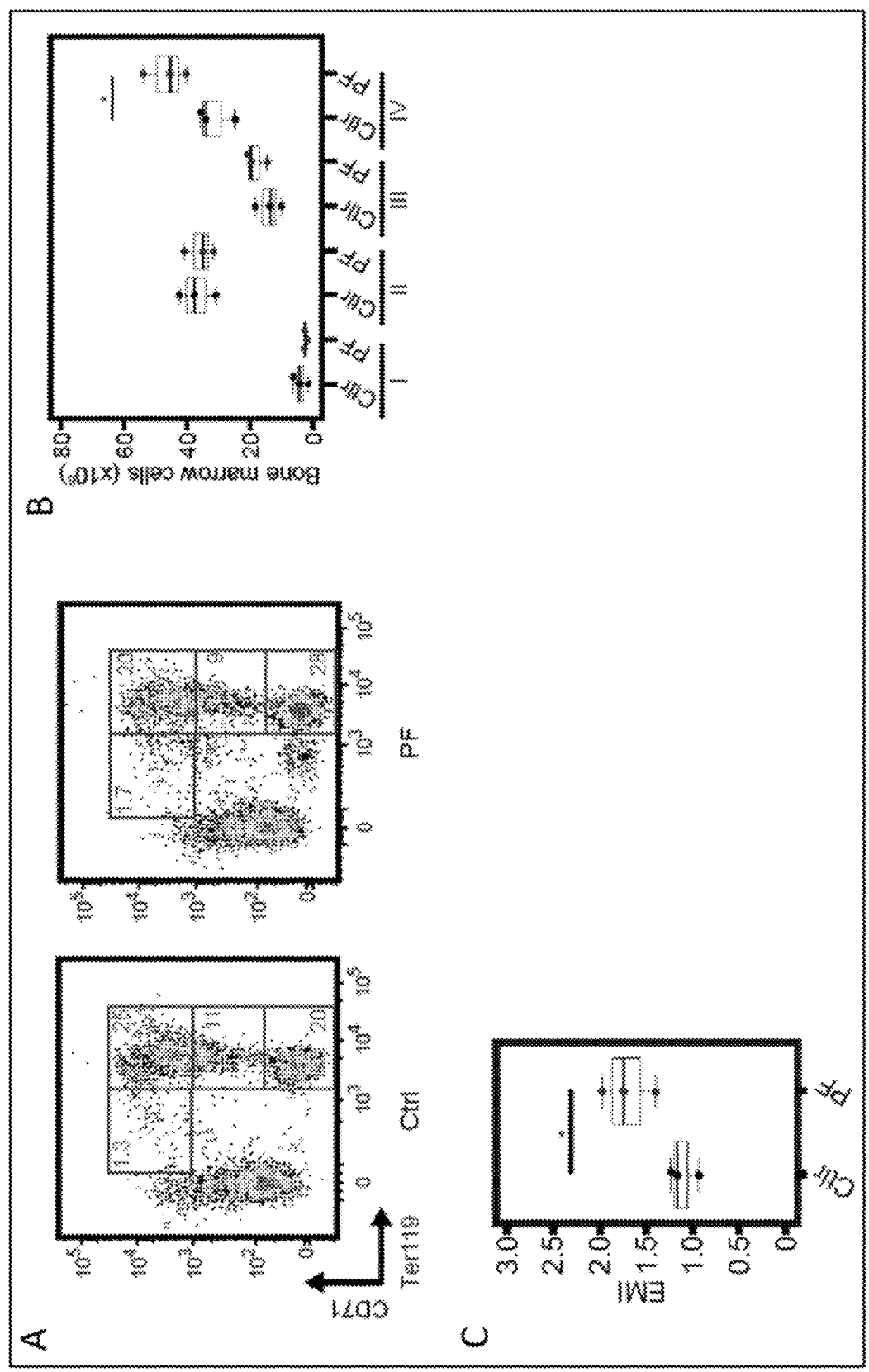
FIG. 10 is the experimental result showing that PF9366 promotes the maturation of erythroblasts. Panels A and B: Bone marrow erythroblasts in each subset analyzed by flow cytometry (Day 2). Representative results of flow cytometric analysis are shown in Panel A. The cumulative cell numbers of the indicated subsets are shown in Panel B. Panel C: Erythroblast maturation index. Asterisk represents *P<0.05.

Additionally, MAT inhibitor PF9366 (PF) was administered to mice and the effect thereof was investigated. Vehicle (DMSO) (control (Ctrl)) or 10 mM PF9366 (prepared at a concentration of 40 μl/40 ml water) was provided in a drinking bottle (0 h). In addition, 80 μl of vehicle (DMSO) or 80 μl of 10 mM PF9366 dissolved in 1 ml PBS was also administered intraperitoneally at 0 h and 24 h. Analysis was carried out at Day 2 (48 h). It was revealed that the increase of erythroblast was initiated from subset III, indicating that the maturation of erythroblasts was significantly up-regulated by PF treatment (Panels A-B of FIG. 10). A significant difference in the erythroblast maturation index was also observed (Panel C of FIG. 10).

Example 3

Figure 3:
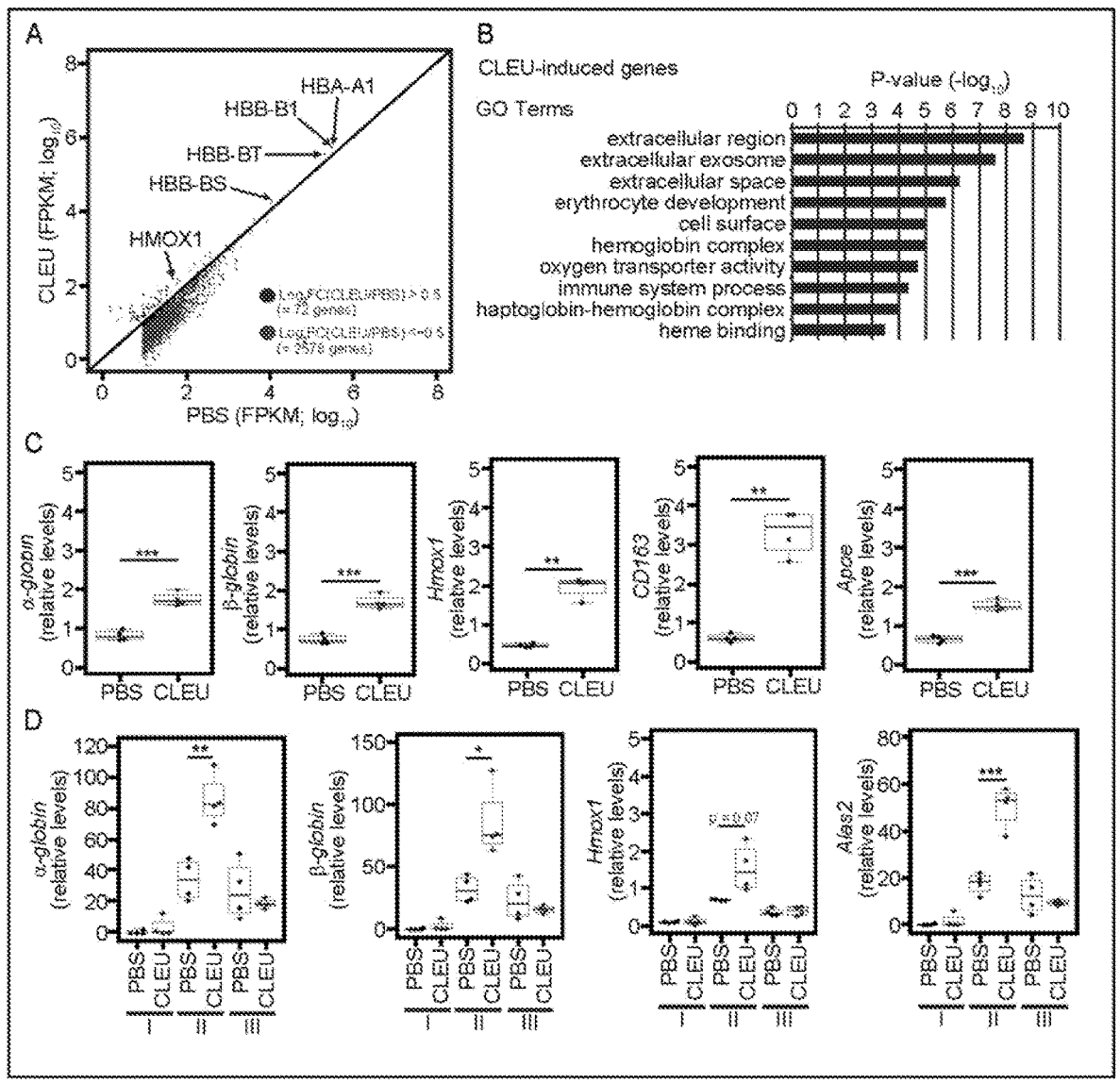
FIG. 3 is the experimental result showing that CLEU treatment strongly induces expression of hemoglobin-related genes in bone marrow erythroblast subset II. Panel A: RNA sequencing results of bone marrow erythroblast subset II from PBS or CLEU treated mouse (Day 2) (CLEU; n=4, PBS; n=4). Exclusively data of genes having FPKM>10 and CV<0.5 (under at least one of the two conditions) and showing the change in expression level ($\log_2$ FC<−0.5 or $\log_2$ FC>0.5, P<0.05) are shown by points. Panel B: Gene ontology (GO) analysis by DAVID 6.8. on genes significantly induced by CLEU treatment. Panel C: To confirm the expression level by the RNA sequencing, the RNA expression levels of genes were measured by RT-PCR analysis and were normalized to Actb. Panel D: RNA expression levels of the indicated genes in the indicated subsets of bone marrow erythroblast obtained by treating with PBS or CLEU (Day 2). Expression levels were normalized to Actb. Each point shown on the box plot corresponds to an individual mouse sample. Asterisks correspond to p values: *$P<0.05$, $P<0.01$, and *$P<0.001$.
Figure 4:
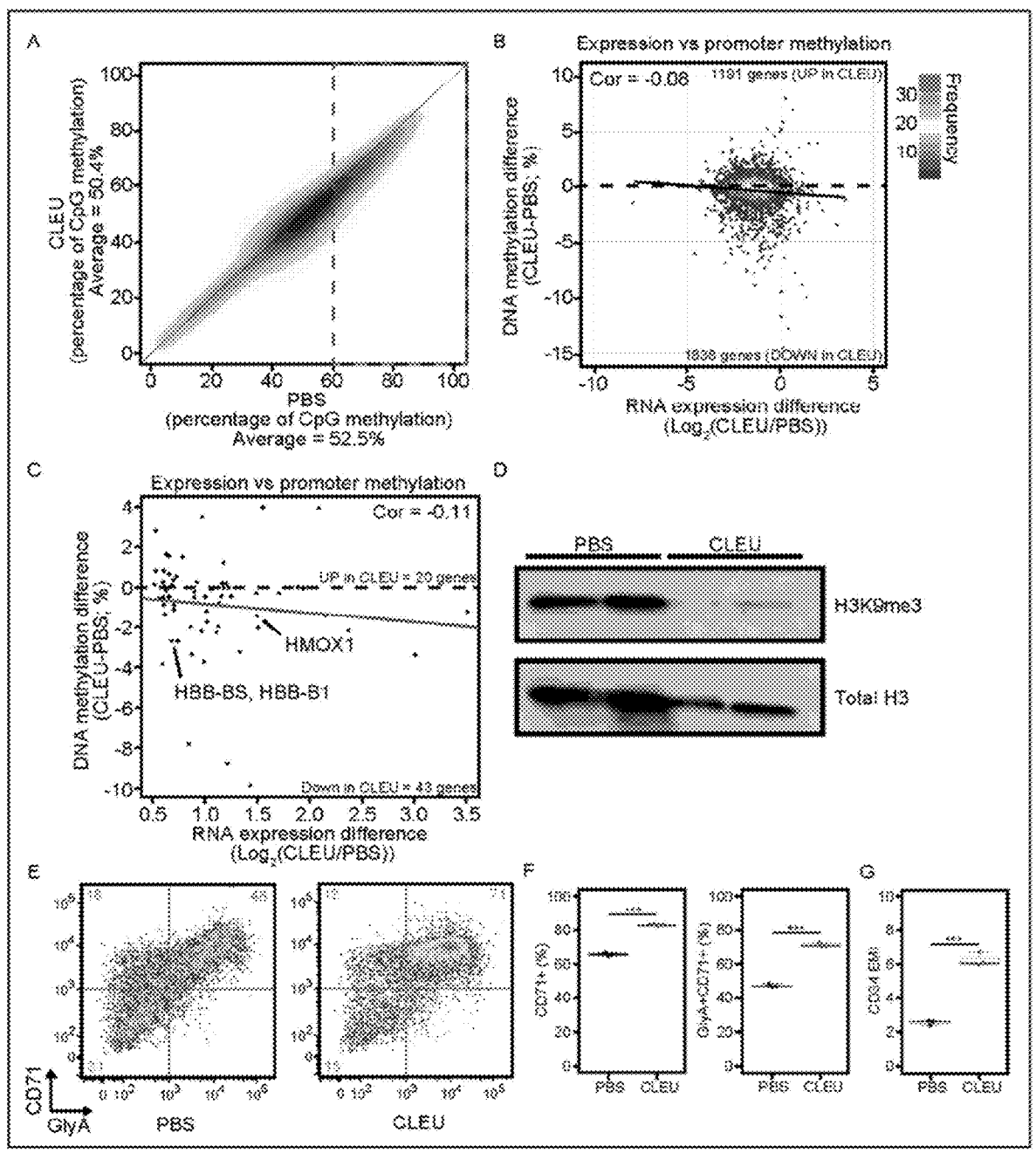
FIG. 4 is the experimental result showing that epigenetic demethylation induces the final maturation of erythroblasts. Panel A: WGBS (whole genome bisulfite sequencing) results of bone marrow erythroblast subset II harvested from CLEU or PBS treated mouse (Day 2) (CLEU; n=2, PBS; n=2). Panel B: Difference in expression levels versus difference in CpG methylation of the promoter for all expressed genes (at least one of FPKM>10 and CV<0.5). The correlation (Cor) was −0.08. Panel C: Difference in expression levels versus difference in CpG methylation of the promoter among genes whose expression were significantly induced. The correlation (Cor) was −0.11. Panel D: Images (photographs) showing western blot (WB) results of trimethylation of lysine 9 of histone H3 (H3K9me3) on bone marrow erythroblast subset II harvested from CLEU or PBS treated mouse (Day 2). Panels E-G: In vitro red blood cell differentiation of Human CD34$^+$ cord blood cells. Panel E: Representative results of flow cytometric analysis. Panel F: Cumulative results for the indicated cell population. Panel G: Cumulative results for CD34 EMI (CD34 red blood cell maturation index: CD71$^+$ GlyA$^+$/CD71$^+$ GlyA$^-$). Each point shown in the box plots represents each technical replicate. Asterisk indicates P<0.001.
Figure 5:
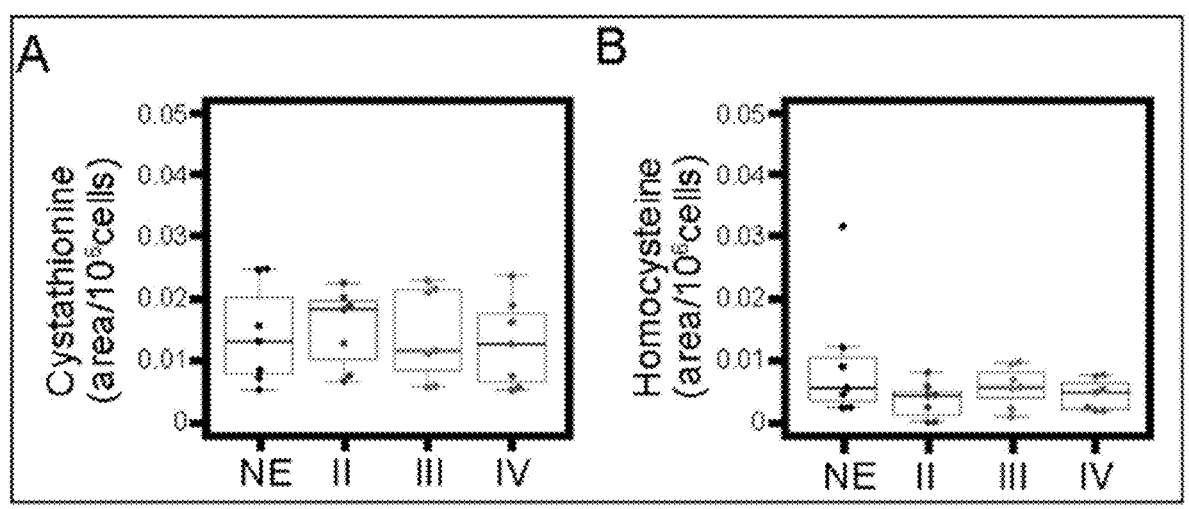
FIG. 5 is the experimental result showing that the abundances of SAM-related metabolites do not change during differentiation and maturation of bone marrow erythroblasts. Panels A and B: Abundances of the indicated metabolites in each of the subsets of cells sorted from bone marrow were analyzed using mass spectrometry. Panel A: cystathionine, Panel B: homocysteine. Each point shown in the box plots represents an individual mouse sample.
Figure 7:
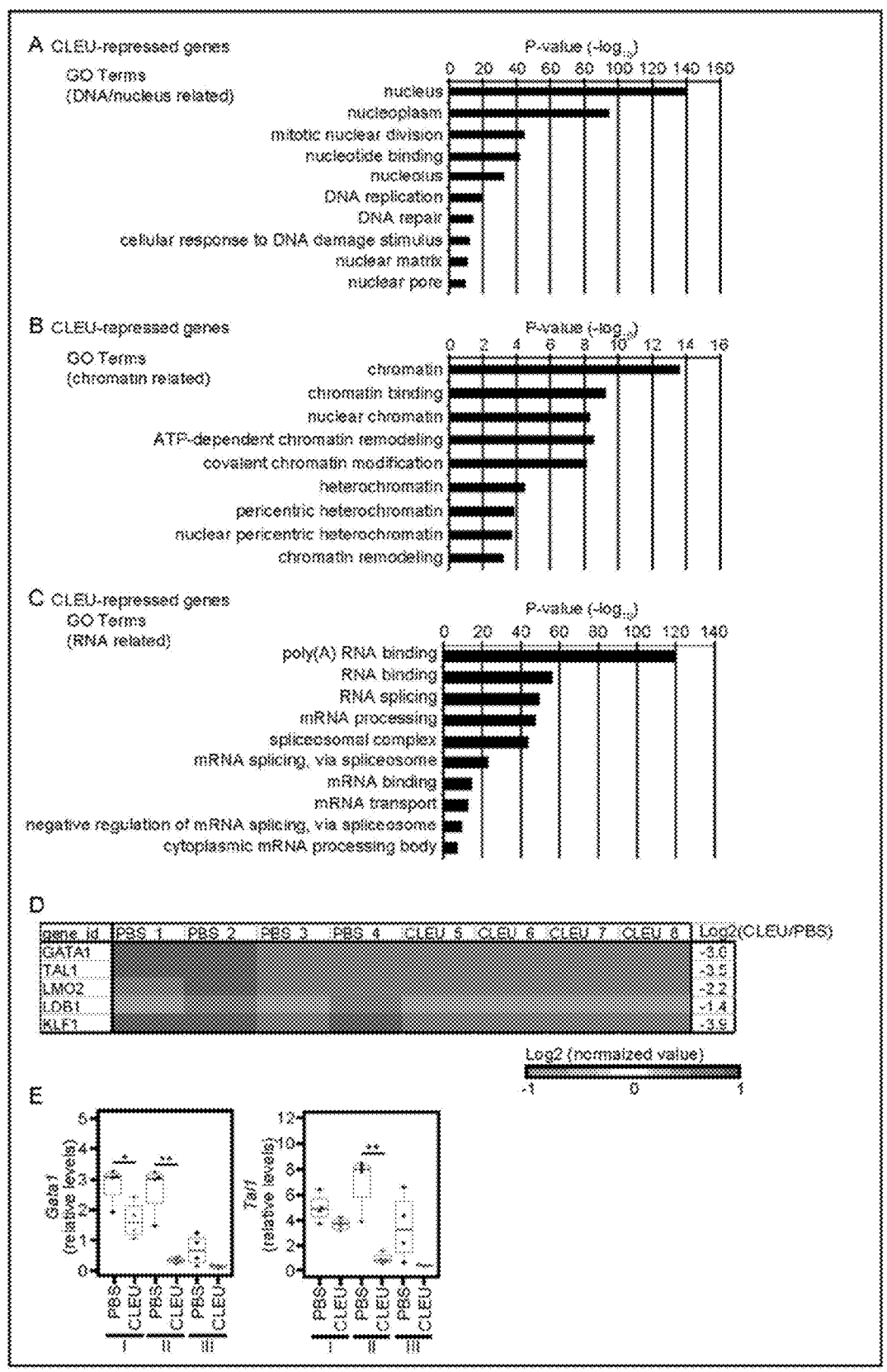
FIG. 7 is the experimental result showing that CLEU treatment induces expression of a group of genes including ribonucleotides and red blood cell transcription factor-related genes. Panels A-C: Gene ontology (GO) analysis by DAVID 6.8. on genes significantly induced by CLEU treatment. Panel A: GO term associated with DNA/nuclei. Panel B: GO term associated with chromatin. Panel C: GO term associated with RNA. Panel D: RNA sequencing results for individual genes in the indicated samples. The expression level for each gene in each sample was normalized to the average FPKM value of the respective gene from the 8 samples. Panel E: RNA expression levels for the respective gene in the indicated subsets of erythroblasts in bone marrow treated with PBS or CLEU (Day 2). Expression levels were normalized to Actb. Each data point shown in the box plots represents an individual mouse sample. Asterisks correspond top values: *P<0.05, P<0.01, and *P<0.001.
Figure 8:
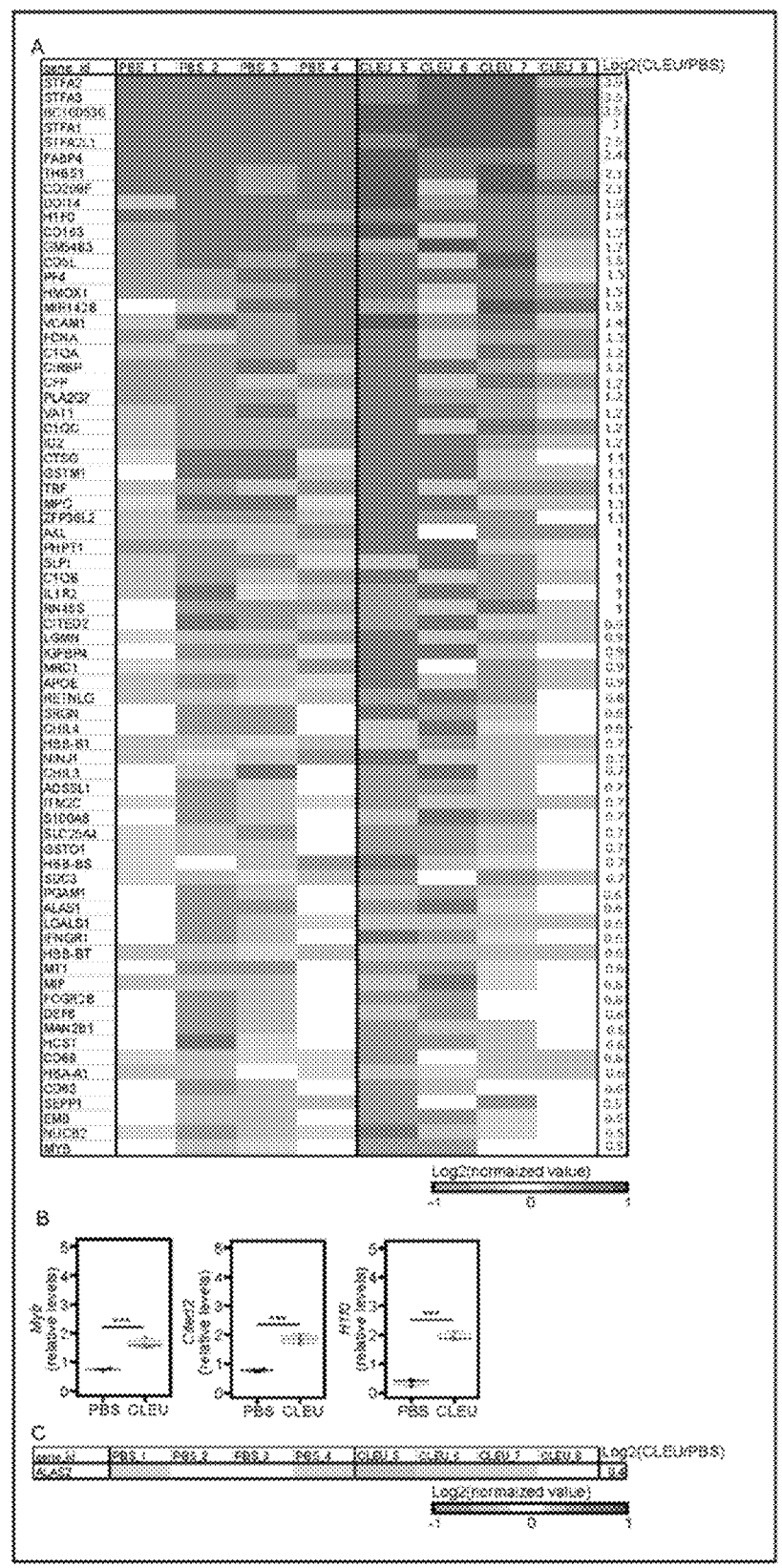
FIG. 8 is the experimental result showing that CLEU treatment induces expression of a group of genes including hematopoietic stem/progenitor cell-related genes. Panel A: RNA sequencing results for the indicated genes in the indicated samples. The expression level for each gene in each sample was normalized to the average FPKM value of the respective gene from the eight samples. Panel B: To confirm the expression level in RNA sequencing, the RNA expression levels of genes shown were measured by RT-PCR analysis and were normalized to Actb. Each data point shown in the box plots represents an individual mouse sample. Asterisk represents P<0.001. Panel C: RNA sequencing results for Alas2 in the indicated samples. The expression level for each gene in each sample was normalized to the average FPKM value of the respective genes from the eight samples.

For the purpose of elucidating the mechanism of the maturation of erythroblasts induced by CLEU treatment, RNA sequencing analysis of BM erythroblast subset II was performed. Although there was no specific morphological difference in nucleated cells among both conditions (Panel E of FIG. 6), significant changes between these conditions in gene expression were observed (Panel F of FIG. 6), and interestingly, it was also observed that most of the individually regulated genes were down-regulated (Panel A of FIG. 3). Gene ontology analysis was performed on these down-regulated genes, and it was revealed that significantly more DNA/nucleus-related genes and/or chromatin-related genes were included in these down-regulated genes (Panels A-B of FIG. 7). These data suggest that such epigenetic changes are involved in dynamic chromatin remodeling that occurs during the final maturation stage where the erythroblasts undergo the final enucleation. In addition, more RNA-related genes were also included in these down-regulated genes (Panel C of FIG. 4), suggesting that RNA processing plays an important role in the maturation of erythroblasts. In addition, transcription factors critical for erythropoiesis, such as Gata1, Tal1, and Klf1, were also significantly down-regulated (Panel D of FIG. 7), indicating that there may be other critical factors governing the final stage of the maturation of erythroblasts. On the other hand, 72 genes were identified as significantly up-regulated (Panel A of FIG. 8). Globin genes were most heavily expressed in CLEU-treated erythroblasts (Panel A of FIG. 3). Gene ontology analysis of these up-regulated genes revealed that, significantly more hemoglobin-related genes and erythropoiesis-related genes as well as extracellular matrix-related genes and immune system-related genes were included (Panel B of FIG. 3), indicating that the contribution of these factors were necessary for effective maturation of erythroblasts. For example, validation analysis confirmed that, not only hemoglobin-related genes but also CD163 (a high-affinity scavenger receptor for the hemoglobin haptoglobin complex) and Apoe were significantly up-regulated (Panel C of FIG. 3). According to previous reports which had shown the contributory role of CD163 and Apoe in erythropoiesis, up-regulation of CD163 and/or Apoe is necessary for proper use of heme and/or lipid membrane synthesis during the maturation of erythroblasts. Furthermore, the expression of Myb and Cited2, known as important transcription factors in differentiation of hematopoietic stem/progenitor cell, as well as the expression of the linker histone component H1f0 were also significantly up-regulated by CLEU treatment (Panel B of FIG. 8), suggesting that they also have some unknown role in the final maturation of erythroblasts. Interestingly, hemoglobin-related gene expression in subset II was significantly up-regulated by CLEU treatment even when compared with the expression in subset III. Such genes also include Alas2 (Panel C of FIG. 8), although Alas2 was not identified above as the up-regulated genes because there were relatively small differences in expression levels between PBS treatment and CLEU treatment. This indicates that such genes are more strongly up-regulated than in the natural maturation process of erythroblasts. Considering the fact that abnormalities in globin genes cause the maturation defects in erythroblasts in disorders such as thalassemia, up-regulation of these genes, on the other hand, could be the driving force for the final maturation stage of erythroblasts.

Example 4

Figure 2:
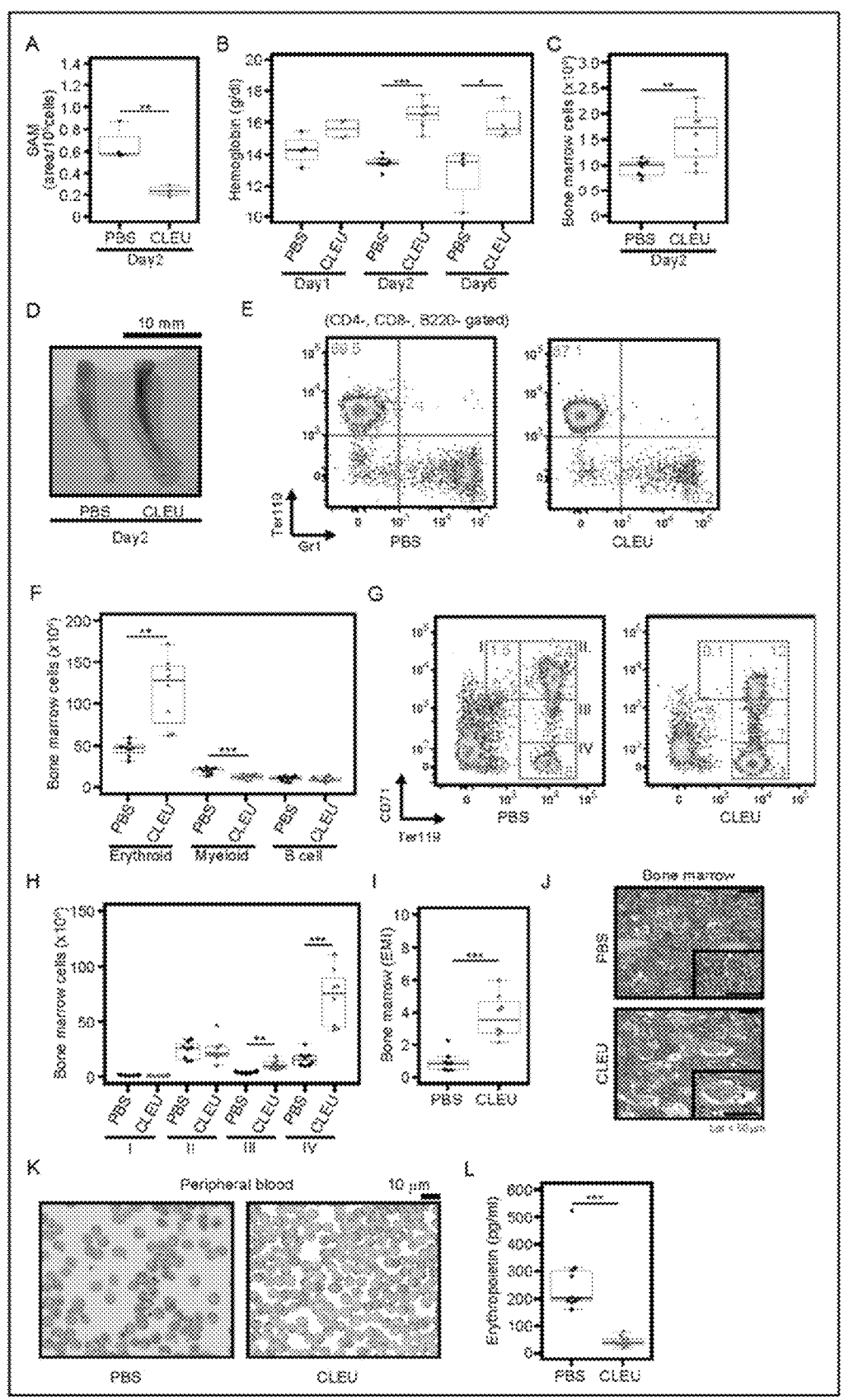
FIG. 2 is the experimental result showing that a significant erythropoiesis was induced independently of erythropoietin as a result of SAM reduction by CLEU. Panel A: Abundance of SAM in cells selected from bone marrow subset II treated with PBS or CLEU (Day 2). Panel B: Peripheral blood hemoglobin concentration on the days indicated after PBS or CLEU treatment. Panel C: Total bone marrow cells harvested from the left and right femur and tibiae of PBS or CLEU treated mouse (Day 2). Panel D: Representative image (photograph) of tibia of PBS or CLEU treated mouse (Day 2). Panels E and F: Matured bone marrow cells from each group analyzed by flow cytometry (Day 2). Representative results of flow cytometric analysis are shown in Panel E. Cumulative cell numbers in each of the indicated groups are shown in F. Red blood cell (Ter119$^+$ Gr1$^-$ B220$^-$ CD4$^-$ CD8$^-$), myeloid (Gr1$^+$ Ter119$^-$ B220$^-$ CD4$^-$ CD8$^-$), and B cells (B220$^+$ Ter119$^-$ Gr1$^-$ CD4$^-$ CD8$^-$). Panels G and H: Numbers of bone marrow erythroblasts in each of the subsets analyzed by flow cytometry (Day 2). Representative results of flow cytometric analysis are shown in Panel G. The cumulative cell numbers in each of the indicated subsets are shown in Panel H. Panel I: Erythroblast maturation index (EMI=III+IV/I+II) of bone marrow harvested from PBS or CLEU treated mouse (Day 2). Panel J: Images (photographs) of hematoxylin and eosin stained bone marrow (Day 2) harvested from PBS or CLEU treated mouse. Panel K: May-Giemsa stained images (photographs) of peripheral blood smear from PBS or CLEU treated mouse (Day 2). Panel L: Serum erythropoietin levels determined by ELISA. Each point shown on the box plot represent to an individual mouse sample. Asterisks correspond to p values: *$P<0.05$, $P<0.01$, and *$P<0.001$.
Figure 9:
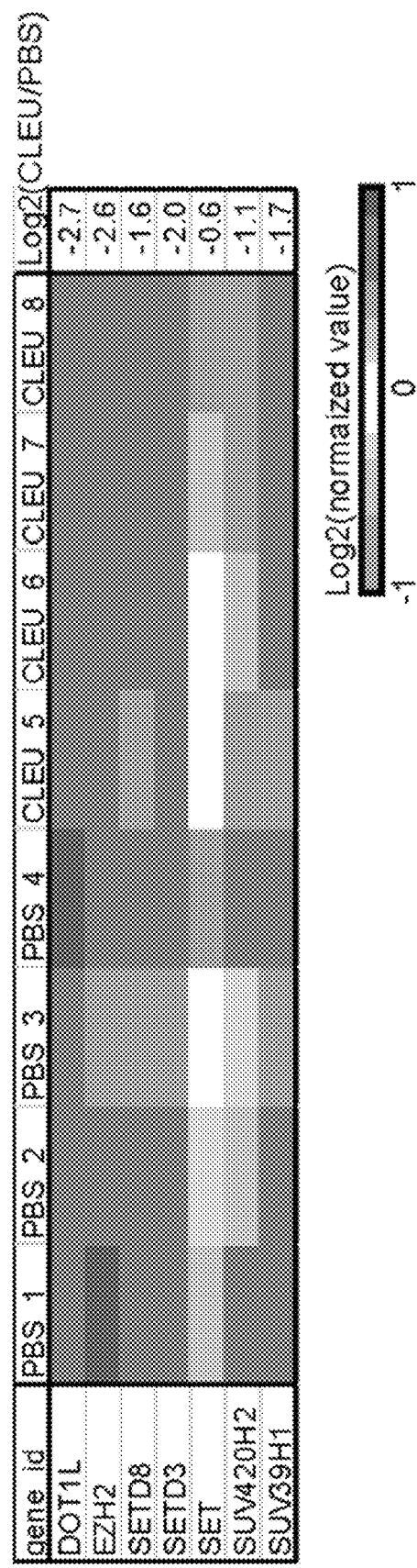
FIG. 9 is the experimental result showing that histone methyltransferase was down-regulated by CLEU treatment. RNA sequencing results for the indicated genes in the indicated samples. The expression level for each gene in each sample was normalized to the average FPKM value of the respective genes from the eight samples.

The overall transcriptional changes observed as above could be attributed to epigenetic modification changes due to the reduced abundance of intracellular SAM (Panel A of FIG. 2). Therefore, in order to elucidate the DNA methylation alteration induced during the maturation of erythroblasts, whole genome bisulfite sequencing (WGBS) was performed. As expected, CLEU treatment reduced DNA CpG methylation by about 2% overall (Panel A of FIG. 4), and the reduction in CpG methylation was more significant in highly methylated genomic regions (Panel A of FIG. 4, red box). As previously observed, the highly methylated genomic regions could be more sensitive to demethylation during the final maturation of erythroblasts. Consistent with the idea that DNA methylation represses gene expression, differences in RNA expression were slightly but negatively correlated with gene promoter CpG methylation (Panel B of FIG. 4). Such correlations were also observed in the significantly up-regulated genes such as β-globin gene and Hmox1 (Panel C of FIG. 4). Furthermore, trimethylation of H3K9, a typical histone methylation marker, was decreased by CLEU treatment (Panel D of FIG. 4). Considering that expression levels of several histone methyltransferase were also significantly down-regulated by CLEU treatment (FIG. 9), the reduction of SAM and repression of the histone methyltransferase could also have contributed to the overall transcriptional changes.

Example 5

Finally, the effect of CLEU on in vitro erythroid cell differentiation conditions of human cord blood CD34$^+$ cells was investigated. In this model, CLEU treatment could induce not only erythroid differentiation but also maturation of human cord blood CD34$^+$ cells (Panels E-G of FIG. 4). This observation demonstrates that the direct effect of CLEU on the maturation of erythroblasts and this mechanism are feasible in the erythropoiesis of human.

Example 6

Figure 12:
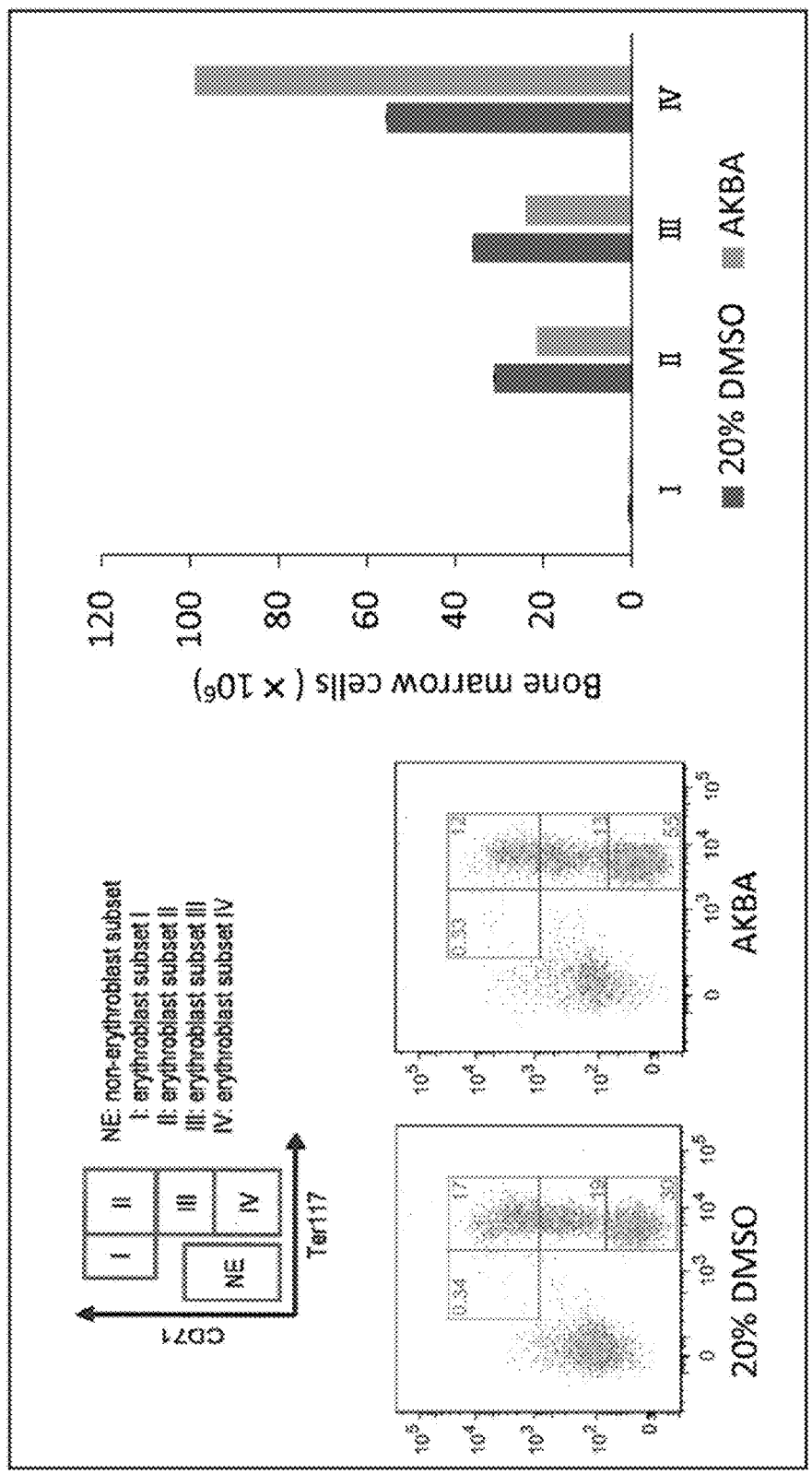
FIG. 12 is the experimental result showing that AKBA promotes the maturation of erythroblasts. Bone marrow erythroblasts in each subset analyzed by flow cytometry (Day 2). Representative results of flow cytometric analysis are shown in the left figure. The cumulative cell numbers of the indicated subsets are shown in the right figure.

MAT inhibitor 3-acetyl-11-keto-β-boswellic acid (AKBA; 2 mg/body) was intraperitoneally administered to mice at 0 and 24 hours, and analyzed after 48 hours. Ter119/CD71 double staining revealed that the maturation of erythroblasts was significantly up-regulated by AKBA treatment (FIG. 12). In addition to CLEU and PF-9366, AKBA also induced the maturation of red blood cells. These similar results obtained from three drugs having different structures suggest that MAT2A inhibitor has an ability to promote erythropoiesis.

To summarize these results, the present study has revealed that the final maturation of erythroblasts is regulated by the level of intracellular SAM that mediates epigenetic modifications. By utilizing this approach, erythropoiesis would be induced in an erythropoietin-independent manner by treating with an S-adenosylmethionine synthase inhibitor such as CLEU. These findings open new ways for future research on erythropoiesis to overcome anemic diseases.

As has been described above, it was demonstrated that the MAT2A inhibitor can be used as a novel therapeutic drug for anemia associated with hematologic disease, which had been difficult to bed treated with conventional hematopoiesis-promoting agents. In addition to cycloleucine, other hematopoiesis-promoting agents may be obtained by identifying compounds targeting MAT2A and more suitable for clinical applications by means of a high-throughput screening system, developing lead compounds from the hit compounds, and verifying their erythropoiesis-promoting effects and safety properties by administering them to a mouse.

INDUSTRIAL APPLICABILITY

The present invention relates to a hematopoiesis-promoting agent useful for medicament, food, and beverage. The present study has developed a new treatment for refractory anemia, which is expected to contribute a reduction in the number of patients with red blood cell transfusion dependency with refractory anemia and the resulting number of patients with iron overload, and of social costs associated with transfusion medicine.

What is claimed is:

1. A method for promoting hematopoiesis comprising administering an S-adenosylmethionine synthetase inhibitor to a subject in need thereof.

2. The method according to claim 1, wherein the S-adenosylmethionine synthetase is methionine adenosyltransferase 2 (MAT2) which is composed of MAT2A and MAT2B.

3. The method according to claim 1, wherein the S-adenosylmethionine synthase inhibitor is selected from the group consisting of cycloleucine, a derivative thereof, a derivative of 4H-s-triazolo[4,3-a][1,4]benzodiazepine, and a pharmaceutically acceptable salt thereof.

4. The method according to claim 1, wherein the S-adenosylmethionine synthase inhibitor is selected from the group consisting of 3-acetyl-11-keto-β-boswellic acid, a derivative thereof, and a pharmaceutically acceptable salt thereof.

5. A method for preventing or treating anemia, comprising administering a hematopoiesis-promoting agent comprising an S-adenosylmethionine synthase inhibitor to a subject in need thereof.

6. The method according to claim 5, wherein the S-adenosylmethionine synthase is MAT2.

7. The method according to claim 5, wherein the S-adenosylmethionine synthase inhibitor is selected from the group consisting of cycloleucine, a derivative thereof, a derivative of 4H-s-triazolo[4,3-a][1,4]benzodiazepine, and a pharmaceutically acceptable salt thereof.

8. The method according to claim 5, wherein the S-adenosylmethionine synthase inhibitor is selected from the group consisting of 3-acetyl-11-keto-β-boswellic acid, a derivative thereof, and a pharmaceutically acceptable salt thereof.

* * * * *